US009297771B2

(12) United States Patent
Fanton et al.

(10) Patent No.: US 9,297,771 B2
(45) Date of Patent: Mar. 29, 2016

(54) METHODS AND SYSTEMS FOR FABRICATING PLATELETS OF A MONOCHROMATOR FOR X-RAY PHOTOELECTRON SPECTROSCOPY

(71) Applicants: Jeffrey T. Fanton, Los Altos, CA (US);
Rodney Smedt, Los Gatos, CA (US);
Bruno W. Schueler, San Jose, CA (US);
David A. Reed, Belmont, CA (US)

(72) Inventors: Jeffrey T. Fanton, Los Altos, CA (US);
Rodney Smedt, Los Gatos, CA (US);
Bruno W. Schueler, San Jose, CA (US);
David A. Reed, Belmont, CA (US)

(73) Assignee: ReVera, Incorporated, Santa Clara, CA (US)

( * ) Notice: Subject to any disclaimer, the term of this patent is extended or adjusted under 35 U.S.C. 154(b) by 298 days.

(21) Appl. No.: 13/975,035

(22) Filed: Aug. 23, 2013

(65) Prior Publication Data
US 2015/0052723 A1 Feb. 26, 2015

(51) Int. Cl.
*G01N 23/20* (2006.01)
*G01N 23/227* (2006.01)
*H01J 37/256* (2006.01)
*G21K 1/06* (2006.01)
*B23Q 17/20* (2006.01)

(52) U.S. Cl.
CPC ............ *G01N 23/20* (2013.01); *G01N 23/2273* (2013.01); *G21K 1/06* (2013.01); *H01J 37/256* (2013.01); *B23Q 17/20* (2013.01); *G21K 2201/064* (2013.01); *Y10T 29/49764* (2015.01); *Y10T 29/49769* (2015.01); *Y10T 29/49771* (2015.01); *Y10T 29/53022* (2015.01)

(58) Field of Classification Search
CPC .................. Y10T 29/49769; Y10T 29/49771; B23Q 17/20; B23Q 17/2404; B23Q 17/2495; B23Q 17/2471; G01N 23/20; G01N 23/20025; G01N 23/20075; G01N 23/2273; G21K 1/06; G21K 1/067
See application file for complete search history.

(56) References Cited

U.S. PATENT DOCUMENTS

| 3,927,319 A | 12/1975 | Wittry |
| 4,599,741 A | 7/1986 | Wittry |
| 5,315,113 A | 5/1994 | Larson et al. |
| 6,055,293 A * | 4/2000 | Secrest ............ G01N 23/20025 378/70 |
| 7,875,857 B2 | 1/2011 | Barnard |
| 2003/0234359 A1 * | 12/2003 | Drown ................... G01N 23/20 250/307 |
| 2013/0077742 A1 | 3/2013 | Schueler et al. |

OTHER PUBLICATIONS

International Search Report and Written Opinion from PCT/US2014/051688 mailed Nov. 24, 2014, 10 pgs.

(Continued)

*Primary Examiner* — Jermie Cozart
(74) *Attorney, Agent, or Firm* — Blakely Sokoloff Taylor Zafman LLP (57) ABSTRACT

Methods and systems for fabricating platelets of a monochromator for X-ray photoelectron spectroscopy (XPS) are disclosed. For example, a method of fabricating a platelet of a monochromator for X-ray photoelectron spectroscopy involves placing a crystal on a stage of an X-ray measuring apparatus, the crystal having a top surface. The method also involves measuring, by X-ray reflection, an orientation of a crystal plane of the crystal, the crystal plane beneath the top surface of the crystal and having a primary axis. The method also involves measuring a surface angle of the top surface of the crystal by measuring a light beam reflected from the top surface of the crystal.

18 Claims, 7 Drawing Sheets

(56) References Cited

OTHER PUBLICATIONS

U. Gelius, et al., A New ESCA Instrument with improved Surface Sensitivity, Fast Imaging Properties and Excellent Energy Resolution, J. of Electron Spectroscopy and Related Phenomena , 52, p. 747 , Elsevier Sci . Pub. B.V. 1990.

T. Ohta et al., Design and Performance of a UHV Compatible Soft X-ray Double Crystal Monochromator at the Photon Factory. Nuclear Instruments and Methods in Physics Research, A246, p. 373, Elsevier Sci. Pub. B.V., 1986.

\* cited by examiner

METHODS AND SYSTEMS FOR FABRICATING PLATELETS OF A MONOCHROMATOR FOR X-RAY PHOTOELECTRON SPECTROSCOPY

BACKGROUND

1) Field

Embodiments of the invention are in the field of X-ray photoelectron spectroscopy (XPS) and, in particular, methods and systems for fabricating platelets of a monochromator for XPS.

2) Description of Related Art

X-ray photoelectron spectroscopy (XPS) is a quantitative spectroscopic technique that measures the elemental composition, empirical formula, chemical state and electronic state of the elements that exist within a material. XPS spectra may be obtained by irradiating a material with a beam of X-rays while simultaneously measuring the kinetic energy and number of electrons that escape from the top, e.g., 1 to 10 nm of the material being analyzed. XPS analysis commonly employs monochromatic aluminum Kα (AlKα) X-rays, which may be generated by bombarding an aluminum anode surface with a focused electron beam. A fraction of the generated AlKα X-rays is then intercepted by a focusing monochromator and a narrow X-ray energy band is focused onto the analysis site on a sample surface. The X-ray flux of the AlKα X-rays at the sample surface depends on the electron beam current, the thickness and integrity of the aluminum anode surface, and crystal quality, size, and stability of the monochromator.

As such, in order to further improve the capabilities of XPS, advances are needed in the area of monochromator fabrication.

SUMMARY

Embodiments of the present invention pertain to methods and systems for fabricating platelets of a monochromator for X-ray photoelectron spectroscopy (XPS).

In an embodiment, a method of fabricating a platelet of a monochromator for X-ray photoelectron spectroscopy involves placing a crystal on a stage of an X-ray measuring apparatus, the crystal having a top surface. The method also involves measuring, by X-ray reflection, an orientation of a crystal plane of the crystal, the crystal plane beneath the top surface of the crystal and having a primary axis. The method also involves measuring a surface angle of the top surface of the crystal by measuring a light beam reflected from the top surface of the crystal.

In an embodiment, an apparatus for providing measurements during a method of fabricating a platelet of a monochromator for X-ray photoelectron spectroscopy includes a stage having a location for placing a crystal thereon. The apparatus also includes an X-ray source and corresponding detector for performing X-ray reflection measurements of a crystal plane of the crystal. The apparatus also includes an autocollimator with a light source for impinging radiation on the crystal and a corresponding detector for measuring a light beam reflected from the crystal.

DETAILED DESCRIPTION

Methods and systems for fabricating platelets of a monochromator for X-ray photoelectron spectroscopy (XPS) are described. In the following description, numerous specific details are set forth, such as XPS system arrangements incorporating a monochromator having quartz platelets, in order to provide a thorough understanding of embodiments of the present invention. It will be apparent to one skilled in the art that embodiments of the present invention may be practiced without these specific details. In other instances, features such as XPS data analysis are not described in detail in order to not unnecessarily obscure embodiments of the present invention. Furthermore, it is to be understood that the various embodiments shown in the Figures are illustrative representations and are not necessarily drawn to scale.

XPS analysis commonly employs monochromatic aluminum Kα (AlKα) X-rays, which may be generated by bombarding an aluminum anode surface with a focused electron beam. The Al-based X-rays are typically focused with a quartz crystal monochromator. XPS signals obtained from samples bombarded with such radiation are typically strong and therefore often provide very meaningful data. However, as mentioned above, in order to further improve the capabilities of XPS, advances are needed in the area of monochromator fabrication. In particular, improvements are needed in the area of quartz platelet fabrication for quartz-based monochromators.

To provide context, performance characteristic of a monochromator fabricated from several quartz crystals, or platelets, can depend on the quality of the individual quartz crystals as well as the crystal orientation consistency of several such crystals. In the former case, monochromator quality can be compromised by localized slope errors or flaws in an individual crystal or platelet. In the latter case, monochromator quality can be compromised by platelet crystal orientation variations in the as-fabricated monochromator. In general, from platelet to platelet, the orientation is determined by the polish. Within a platelet, the orientation consistency is largely determined by the quartz quality.

Figure 1:
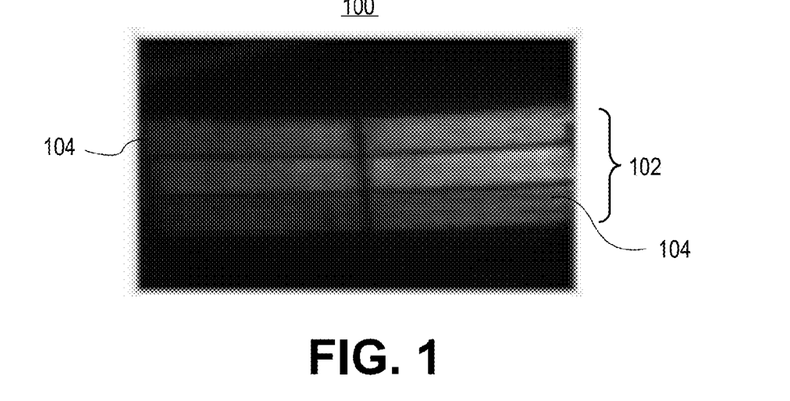
FIG. 1 is an image of reflected Al Kα x-rays from a monochromator based on six individual crystals or platelets grouped on a common substrate, in accordance with an embodiment of the present invention.

In an exemplary embodiment, individual quartz crystals or platelets are bonded to a common substrate for monochromator manufacture. Optical contact is typically performed to ensure that the bonded crystals strictly conform to the precision surface of the monochromator substrate (e.g., typically an elliptical surface). In an example, each of the crystals or platelets is thinned to approximately 60 microns to handle any associated bend stress (e.g., stress from contacting them to a curved substrate). FIG. 1 is an image 100 of reflected light from a monochromator 102 based on six individual crystals or platelets 104 grouped on a common substrate, in accordance with an embodiment of the present invention. The individual crystals are each axis-aligned normal to the quartz surface and, as such, each crystal is individually aligned to provide each platelet of the monochromator 102. In the case that the crystals of the resulting platelets are mis-oriented, then blur from the monochromator occurs.

Figure 2A:
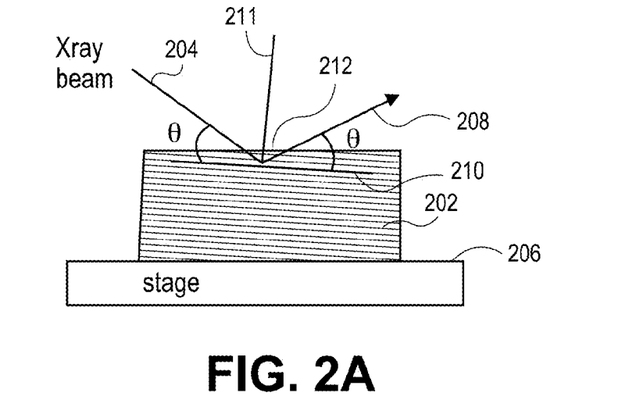
FIGS. 2A and 2B illustrate schematic cross-sectional views of conventional measurements made during the manufacture of an individual quartz crystal for ultimate monochromator fabrication.
Figure 2B:
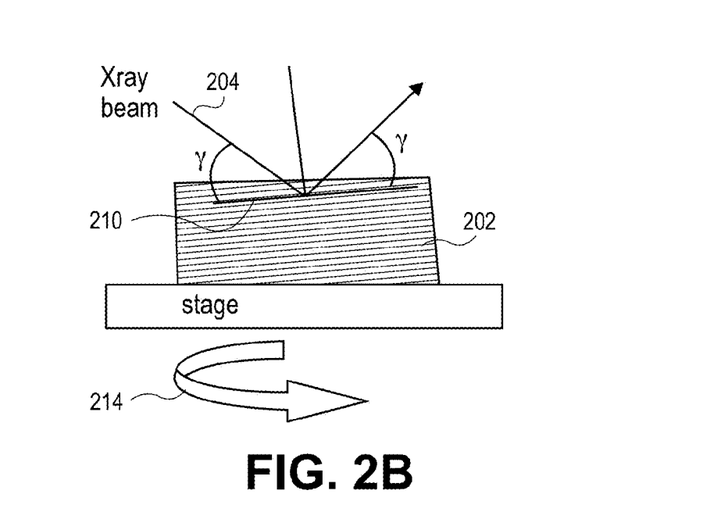

To aid in illustration of one or more embodiments described herein, FIGS. 2A and 2B illustrate schematic cross-sectional views of conventional measurements made during the manufacture of an individual quartz crystal for ultimate monochromator fabrication. Referring to FIG. 2A, crystal orientation is determined by measuring a crystal 202 with an X-ray beam 204 relative to a surface 206, e.g., relative to an uppermost surface of a stage. A reflected X-ray beam 208 subtends a crystal plane 210 within the crystal 202 with the same angle θ to as the incoming x-ray beam 204. In such a measurement, the surface 212 of the crystal (e.g., the orientation of the surface 212 to the surface 206) is irrelevant. That is, normal 211 for the measurement is oriented to the crystal plane 210.

Referring again to FIG. 2A, the complete measurement is made by first recording the angle θ of the reflected beam. Then, referring to FIG. 2B, the crystal 202 is rotated 180 degrees, e.g., by rotating 214 the stage. Once rotated, the X-ray beam 204 is again impinged on the crystal 202 to determine an angle γ. The difference of the two angular measurements (i.e., the difference between θ and γ) provides information regarding the angle of the crystal planes 210 of the crystal 202 relative to the stage surface 206 (or equivalently, the bottom surface of the crystal 202). If the angles both read exactly the same, the planes are perfectly parallel to the stage surface 206. However, if the angles differ by 1°, then the planes are off 0.5°, etc. It is to be understood that the above described arrangement provides the orientation in the L-R direction. The orthogonal orientation is measured by comparing angles with the stage at 90° and 270°. Nonetheless, the above described measurement is based on the assumption that the stage rotation is perfect, which is rarely the case, particularly within an error of less than 1 arcsec level for high quality monochromator manufacturing.

In accordance with an embodiment of the present invention, crystal orientation is measured relative to a stage surface using an autocollimator during the above described orientation determination. In one such embodiment, an autocollimator is combined with a system used for measuring relative crystal plane orientation to determine the quality of a measured crystal in the preparation of the crystal for inclusion in a monochromator as a high quality platelet. The autocollimator can be used to provide a reading of the surface angle of the crystal, e.g., in addition to the crystal plane angle information described above. In one such embodiment, in order to obtain high quality surface information, a reflective layer is added to the surface of the crystal. However, the reflectively layer is kept sufficiently thin to not hinder the above described X-ray measurements. In other embodiments, a reflective layer is not used.

Figure 3A:
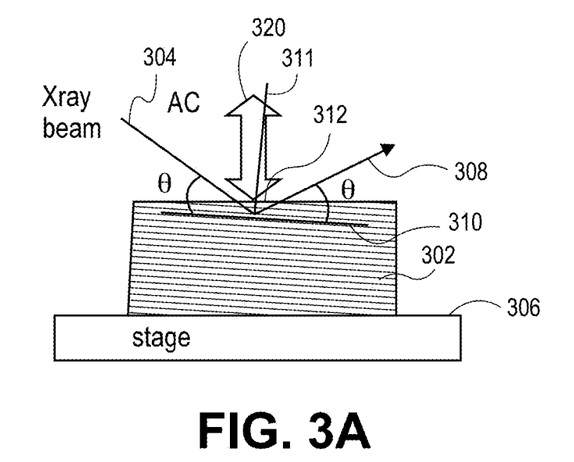
FIGS. 3A and 3B illustrate schematic cross-sectional views of measurements made during the manufacture of an individual quartz crystal for ultimate monochromator fabrication, in accordance with an embodiment of the present invention.
Figure 3B:
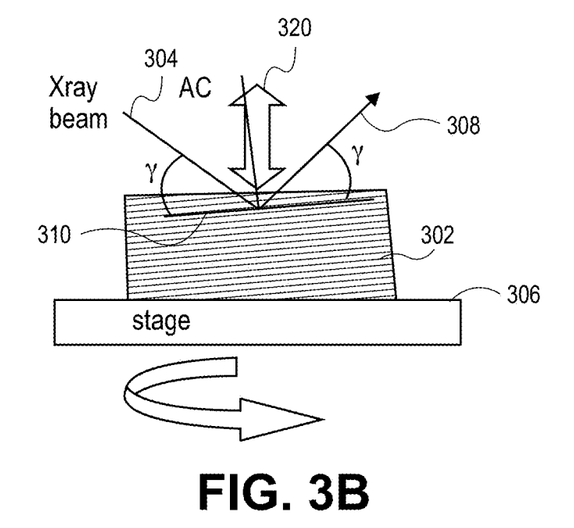

As a general example, FIGS. 3A and 3B illustrate schematic cross-sectional views of measurements made during the manufacture of an individual quartz crystal for ultimate monochromator fabrication, in accordance with an embodiment of the present invention. Referring to FIG. 3A, orientation of the planes 310 internal to a crystal 302 is measured with an X-ray beam 304. A reflected X-ray beam 308 subtends a crystal plane 310 within the crystal 302 with the same angle θ to as the incoming x-ray beam 304. As described above, in such a measurement, the surface 312 of the crystal 302 (e.g., the orientation of the surface 312 to an underlying surface 306) does not play a role in the X-ray measurement. That is, normal 311 for the measurement is oriented to the crystal plane 310. Additionally, referring again to FIG. 3A, an autocollimator (AC) measurement 320 is made to determine an angle of a reflected beam of the AC relative to an angle of the surface 312 as measured by the AC.

Then, referring to FIG. 3B, an underlying stage is rotated 180 degrees and the above measurements (both X-ray and AC) are repeated. As a result, information regarding an X-ray angle relative to the AC surface measurement is provided for at least two orientations. The difference between the measurements at the relative positions of FIGS. 3A and 3B provides the orientation of crystal plane 310 relative to the surface 312 of the crystal 302. Essentially, then, any requirements that an underlying stage be perfect and are eliminated and now accounted for with the surface 312 angle measurements. That is, the conventional measuring of crystal planes described in association with FIGS. 2A and 2B as assumed against the bottom of the crystal resting on a perfectly flat underlying stage (perfect-stage scenario) is replaced with measurement against an angle relative to the top surface 312 of the crystal 302. It is to be understood that, even if the AC is not perfectly aligned with an underlying stage, the measurements of crystal plane and crystal surface orientation will not be impacted since measurements are taken at more than one stage orientation.

Figure 4A:
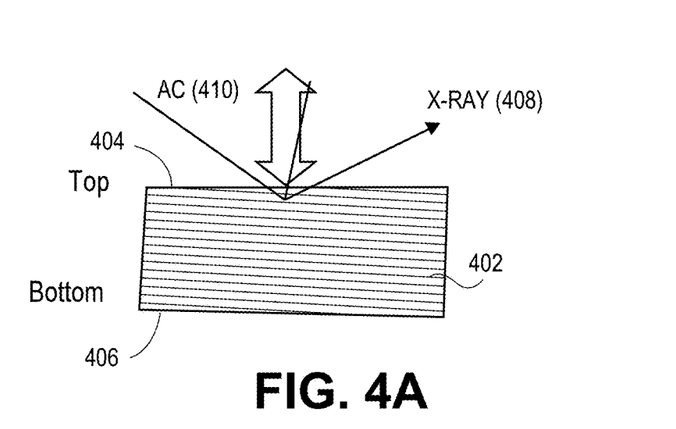
FIGS. 4A-4D illustrate schematic cross-sectional views of measurements made during the manufacture of an individual quartz crystal for ultimate monochromator fabrication, in accordance with an embodiment of the present invention.

As a more specific example, FIGS. 4A-4D illustrate schematic cross-sectional views of measurements made during the manufacture of an individual quartz crystal for ultimate monochromator fabrication, in accordance with an embodiment of the present invention. Referring to FIG. 4A, a crystal 402 has a top surface 404 and a bottom surface 406. An X-ray measurement 408 is made to determine crystal plane orientation internal to the crystal 402, without influence from the orientation of surface 404. An autocollimator (AC) measurement 410 is also made to determine orientation of the surface 404, e.g., relative to the bottom surface 406. As such, both AC and X-ray information (and, hence, AC information relative to X-ray information) is obtained for crystal 402 at a first position of the crystal 402.

In an embodiment, in order to obtain good reflection data from surface 404 for AC measurement 410, a reflective coating (e.g., a silver coating) is first formed on the surface 404. In one such embodiment, the reflective coating is maintained sufficiently thin to not interfere with X-ray measurement 408. It is to be understood, however, that for an opaque material, such as InSb, a reflective coating may not be necessary.

In an embodiment, referring again to FIG. 4A, four such measurements are taken at 90 degree intervals in order to remove the delta between the X-ray and AC coordinate system. For example, the absolute delta in x-direction is the delta X-ray minus AC for 0° and 180°. For y-direction, the absolute delta X-ray minus AC at 90° and 270°. More generally, in an embodiment, measuring with X-ray and AC involves performing first and second X-ray reflection measurements at approximately 180 degrees to one another. In one such embodiment, the measuring further involves performing third and fourth X-ray reflection measurements at approximately 180 degrees to one another, and orthogonal to the first and second X-ray reflection measurements. In an embodiment, measuring the surface angle of the top surface 404 of the crystal 402 enables accommodating for rocking of the crystal 402 on a stage (e.g., the stage shown in FIGS. 3A and 3B) during the measuring of the orientation of the internal crystal planes of the crystal.

Thus, in an embodiment, referring in general to FIG. 4A in association with FIGS. 3A and 3B, a method of fabricating a platelet for a monochromator involves placing a crystal 402 on a stage of an X-ray measuring apparatus. The crystal 402 has a top surface 402 with a reflective layer disposed thereon. An orientation of a crystal plane of the crystal 402 is measured by X-ray reflection 408, where the crystal plane is beneath the top surface of the crystal 402 and has a primary axis. The method also involves measuring a surface angle of the top surface of the crystal by measuring a light beam reflected from the reflective layer disposed on the top surface of the crystal 402, e.g., by an AC measurement 410. In one such embodiment, the surface angle of the top surface of the crystal 402 is measured while measuring the orientation of the crystal plane by X-ray reflection. The measurements can be made at several different rotational positions of a stage or other underlying surface. In an embodiment, the measurements enable determination of an angle between the top surface 404 and the primary axis of the crystal plane of the crystal 402. In a specific such embodiment, if the angle between the top surface and the primary axis of the crystal plane is approximately normal or at unity, the reflective layer is removed from the crystal to provide a platelet for monochromator fabrication. If, however, the angle between the top surface and the primary axis of the crystal plane is not approximately normal or at unity, polishing of the crystal may be needed, as described below.

Figure 4B:
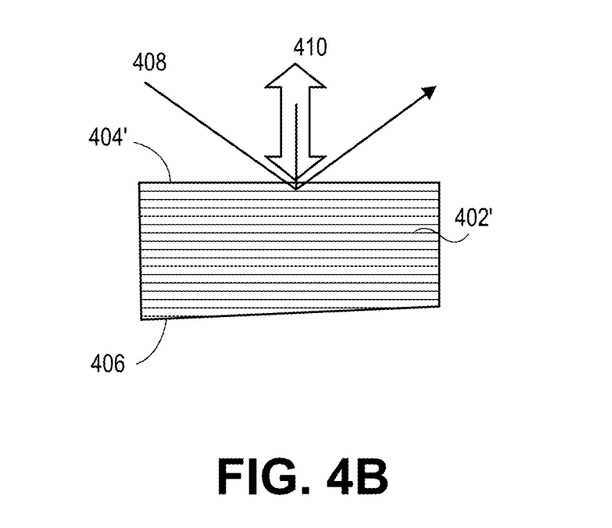

Referring to FIG. 4B, the crystal 402 of FIG. 4A is adjusted by polishing top surface 404 until the X-ray measurement 408 and the AC measurement 410 agree to unity. This operation provides a new top surface 404' for an adjusted crystal 402'. The process may involve several iterations of the measurements described in association with FIG. 4A, as depicted in FIG. 4B. In an embodiment, since the polishing is performed at the top surface 404, a reflective coating layer may need to be redeposited for each iteration. At this stage in the fabrication, in an embodiment, the bottom surface 406 may not be parallel to the polished top surface 404', as is depicted.

Thus, in an embodiment, the angle between the top surface and the primary axis of the crystal plane is not approximately normal or at unity as described in association with FIG. 4A, at least a portion of the top surface 404 of the crystal 402 is removed to provide a modified crystal 402' having a second top surface 404'. In one such embodiment, a second reflective layer is formed on the second top surface 404' of the modified crystal 402'. The measurements described in association with FIG. 4A are then repeated. The process may be reiterated until the angle between the top surface and the primary axis of the crystal plane is approximately normal or at unity.

Referring again to FIGS. 4A and 4B, a surface 404 measurement is performed by measuring a light beam reflected from a reflective layer by impinging radiation from a light source of an autocollimator on the reflective layer. In one such embodiment, the impinging radiation is aligned normal to the stage of an X-ray measuring apparatus. In a specific such embodiment, visible light is emitted from the light source of the collimator.

Figure 4C:
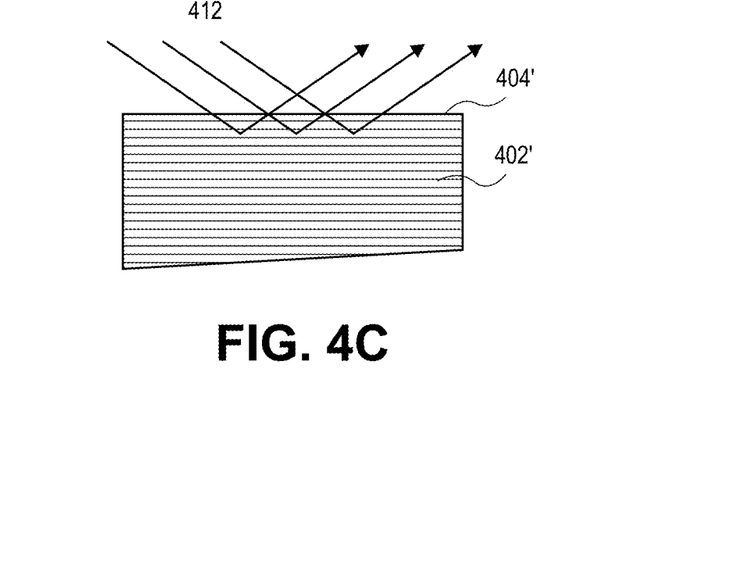

Referring to FIG. 4C, in an embodiment, topography of the new surface 404' is measured by a topographical measurement 412. For example, although the polished surface 404' may provide a global surface where an X-ray measurement and an AC measurement of the surface 404' agree to unity, smaller topographical imperfections may be removed at this point to ensure global uniformity. It is to be understood that there may be little that can be done to fix or remove imperfections within a single crystal. Nonetheless, in one embodiment, it is still valuable to check uniformity across the crystal prior to contacting the crystal to a substrate for monochromator fabrication, e.g., in the case that the crystal is not suitable for use.

Figure 4D:
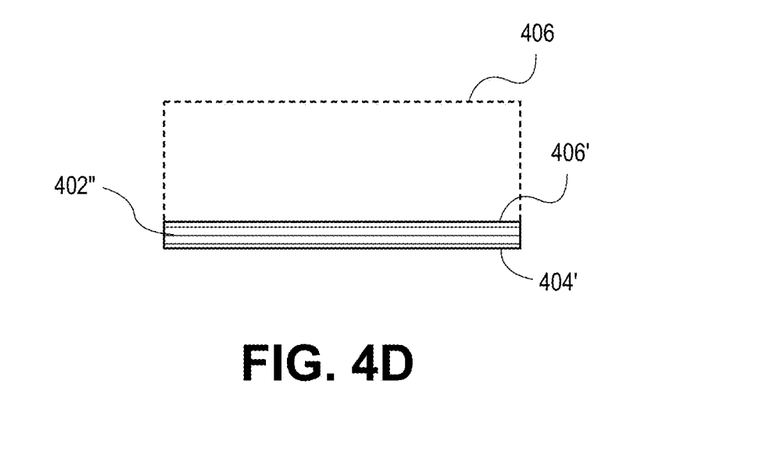

Referring to FIG. 4D, the adjusted crystal 402' having the new top surface 404' is polished from the bottom surface 406 to provide new bottom surface 406' of a thinned, and properly oriented, crystal or platelet 402". In an embodiment, the adjusted crystal 402' is flipped and is thinned from the bottom surface 406 and made parallel to the top surface 404'. In one such embodiment, the thinning is ensured to be parallel by using interferometric feedback during the thinning. The crystal or platelet 402" thus has internal planes that are parallel with the surfaces 404' and 406'.

Thus, in an embodiment, a method of fabricating a platelet for a monochromator involves thinning the modified crystal 402' from a bottom surface 406 of the modified crystal 402' opposite the second top surface 404' to render a new bottom surface 406' parallel with the second top surface 404' based on interferometric feedback. In an embodiment, then, both the top and bottom surface of a crystal are modified. In another embodiment, however, only the bottom surface is modified. For example, in one such embodiment, in the case the angle between the top surface and the primary axis of the crystal plane is approximately normal or at unity at the initial measurements of FIG. 4A, operations described in association with FIG. 4B are omitted and prior to fabricating the monochromator, only the bottom surface of the crystal is thinned to render the bottom surface parallel with the top surface. The thinning may be based on interferometric feedback.

Figure 5:
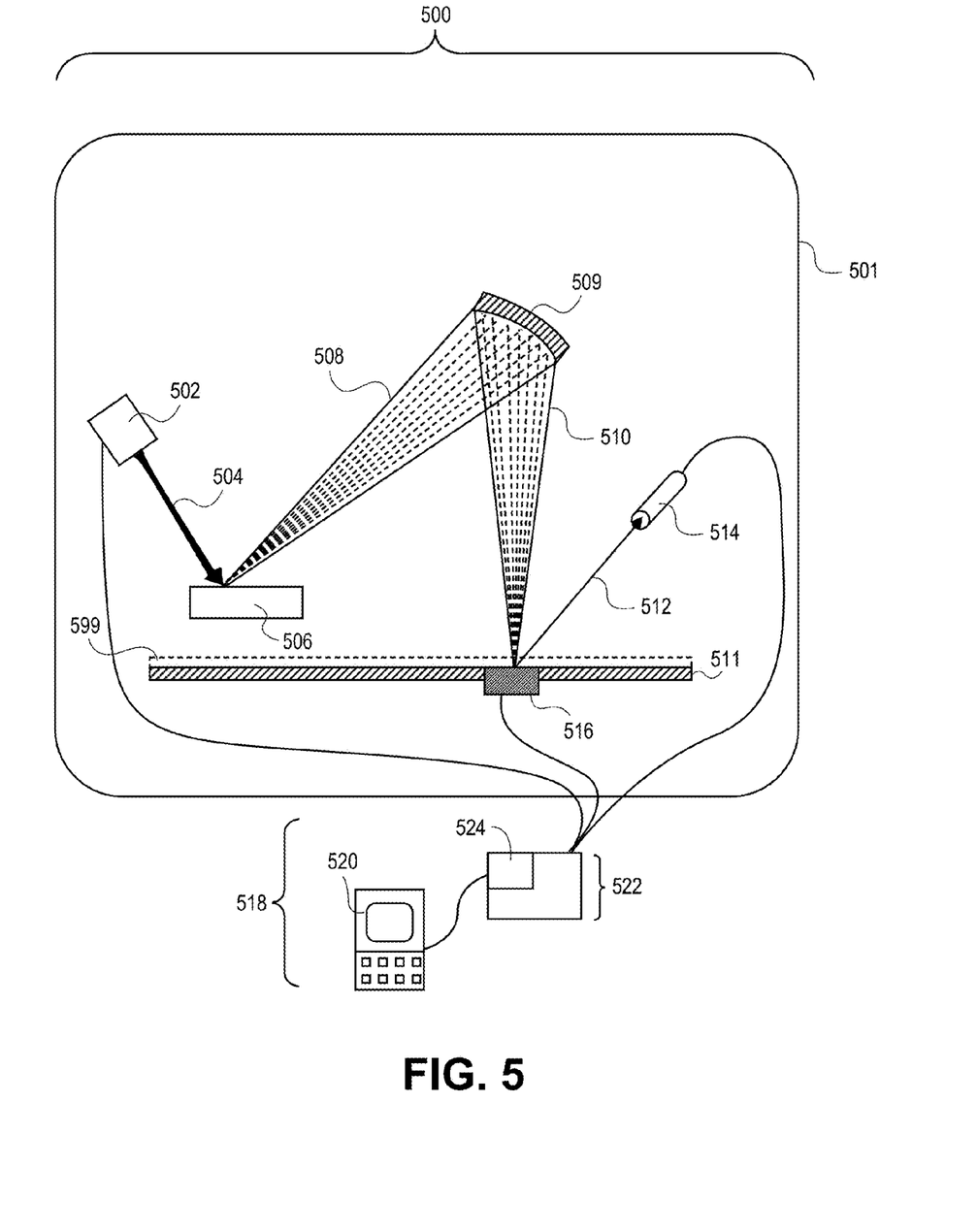
FIG. 5 is an illustration representing a film measurement system having XPS detection capability and a monochromator, in accordance with an embodiment of the present invention.

In an aspect of the present invention, an XPS system includes a monochromator having platelets fabricated by an approaches described herein. For example, FIG. 5 is an illustration representing a film measurement system having XPS detection capability, in accordance with an embodiment of the present invention. It is to be understood that the XPS system described below is one exemplary system where a monochromator described herein may be used. Other systems may equally benefit, or even benefit to a greater extent, from one or more embodiments described herein. For example, an XRF measurement system may include a like monochromator. And, in some cases, the XRF can be more sensitive to monochromator blur than the XPS measurement system described below.

Referring to FIG. 5, a film measurement system 500 includes an XPS generation and detection system housed in a chamber 501 coupled with a computing system 518. The XPS generation and detection system includes an electron beam source 502 provided for generating an electron beam 504. Electron beam 504 is used to generate an X-ray beam 508 by bombarding an anode 506. A monochromator 509 is provided for focusing a monochromatized X-ray beam 510 from X-ray beam 508. A sample holder 511 may be used to position a sample 599 in a pathway of monochromatized X-ray beam 510. An XPS detector 514 is provided for collecting an XPS signal 512 generated by bombarding sample 599 with monochromatized X-ray beam 510. Computing system 518 may include a user interface 520 coupled with a computing portion 522 having a memory portion 524.

Additionally, a flux detector 516 may be provided for determining an estimated flux of monochromatized X-ray beam 510. In one such embodiment, flux detector 516 is positioned at sample holder 511, as depicted in FIG. 5. In an embodiment Flux detector 521 is used to provide a proxy X-ray flux measurement for Flux detector 520 for estimated flux of monochromatized X-ray beam 510. By positioning flux detector 521 at near the monochromator to intersect a small portion of the primary X-ray flux above the sample 511, the primary X-ray flux can be monitored while the monochromatized X-ray beam 510 meets sample holder 511, as depicted in FIG. 5.

In an embodiment, and in order to address one or more of the above described issues with monochromator 509 fabrication, an auto-collimator is used in the manufacture of individual crystals or platelets, e.g., in the manufacture of quartz crystals or platelets. In one such embodiment, the monochromator 509 of FIG. 5 is fabricated from several such platelets. In a particular embodiment, the monochromator 509 has a total crystal surface area of approximately 140 mm×48 mm, and a total blur of the monochromator is less than approximately 5 microns. In one embodiment, absolute alignment of the crystals or platelets to surface normal is less than approximately 50 μrad (e.g., approximately 1.5 microns of blur). In one embodiment, consistency of the planes in the quartz platelets is less than approximately 5 μrad (e.g., 2 microns of blur). In a particular embodiment, the above blur-related values are suitable for a monochromator having a focal length of the optic or approximately 200 mm.

In an aspect of the invention, an XPS measurement may be made upon introduction of a sample into the XPS system 500. The sample is bombarded with a monochromatized (by monochromator 500) X-ray beam. In response to bombardment by the X-ray beam, an XPS signal (composed of photoelectrons) is emitted from the sample and collected in a detector. In an embodiment, the XPS signal is correlated with the atomic dose of a particular atomic species in the sample. In one embodiment, the atomic dose is correlated with a sample property such as, but not limited to, the thickness of a film in the sample, the depth to which the particular atomic species is incorporated into the sample or a concentration ratio of several atomic species in the sample.

Figure 6A:
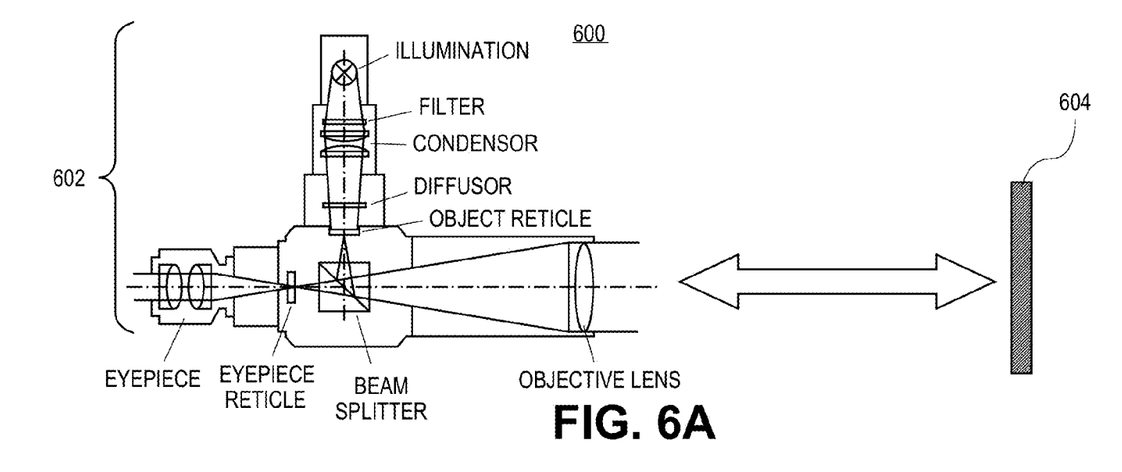
FIG. 6A illustrates a schematic of a system for performing an autocollimator measurement of a surface of a crystal for use in a monochromator, in accordance with an embodiment of the present invention.

In another aspect, embodiments of the present invention may not be limited to the use of autocollimator-based measurements. As a reference point, however, FIG. 6A illustrates a schematic of a system 600 for performing an autocollimator measurement of a surface of a crystal for use in a monochromator, in accordance with an embodiment of the present invention. Referring to FIG. 6A, an autocollimator 602 is used to measure a surface angle of a sample 604. As is seen in FIG. 6A, the measurement is typically performed essentially, if not perfectly, normal to the measured surface of the sample 604. A convenience of using an autocollimator may be the ready commercial availability of such a measuring apparatus. One of ordinary skill in the art will appreciate that, in optics, a "collimator" refers to a lens or set of lenses/mirrors that converts a diverging beam into a parallel beam. In other instances, the term may be used to refer to a set of lenses that shrink or expand an existing collimated beam into another collimated beam of a different diameter. In an embodiment, the term, "autocollimator" refers to a specific instrument that is used to measure surface angles.

Figure 6B:
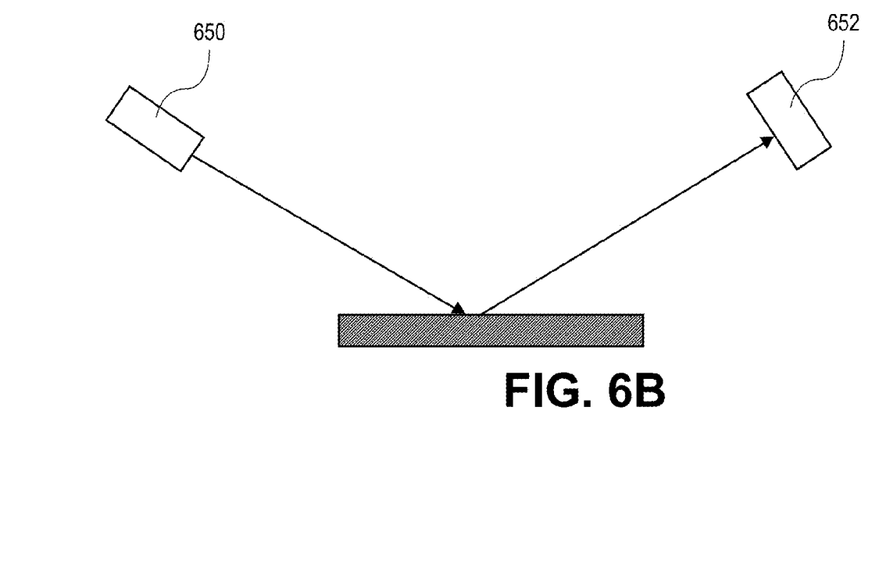
FIG. 6B illustrates a schematic of a system for performing an oblique measurement of a surface of a crystal for use in a monochromator, in accordance with another embodiment of the present invention.

In other embodiments, in place of an autocollimator, systems based on oblique angle surface measurements may be used. For example, FIG. 6B illustrates a schematic of a system for performing an oblique measurement of a surface of a crystal for use in a monochromator, in accordance with another embodiment of the present invention. Referring to FIG. 6B, a laser 650 is used at an angle other than normal to introduce light on a surface which is reflected and collected at a position-sensitive detector 652. That is, if surface measurement apparatus other than an autocollimator is used, non-normal angle measurements may be made to determine surface angles for a sample. Thus, more generally, in addition to autocollimator measurements, other optical techniques may be used. In essence, any suitable approach may be used where an optical technique provides information regarding surface orientation, while the X-ray measurements provide information regarding crystal plane orientation.

In a particular embodiment, however, an apparatus for providing measurements during a method of fabricating a platelet of a monochromator for X-ray photoelectron spectroscopy includes a stage having a location for placing a crystal thereon. An X-ray source and corresponding detector for performing X-ray reflection measurements of a crystal plane of the crystal is also included. An autocollimator is provided with a light source for impinging radiation on the crystal, along with a corresponding detector for measuring a light beam reflected from the crystal. In one such embodiment, the autocollimator is aligned normal to the stage. In one embodiment, the light source is a visible light source. In an embodiment, the above arrangement enables use of an imperfect stage. The autocollimator measurements can be used to confirm that no crystal tipping occurred during X-ray measurement, instead of relying on or making assumptions based on an idealized stage.

In an embodiment, the above described crystal measuring apparatus, or similar apparatus, further includes a computer system coupled to the corresponding detector of the X-ray source and the corresponding detector of the autocollimator. Thus, embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 7:
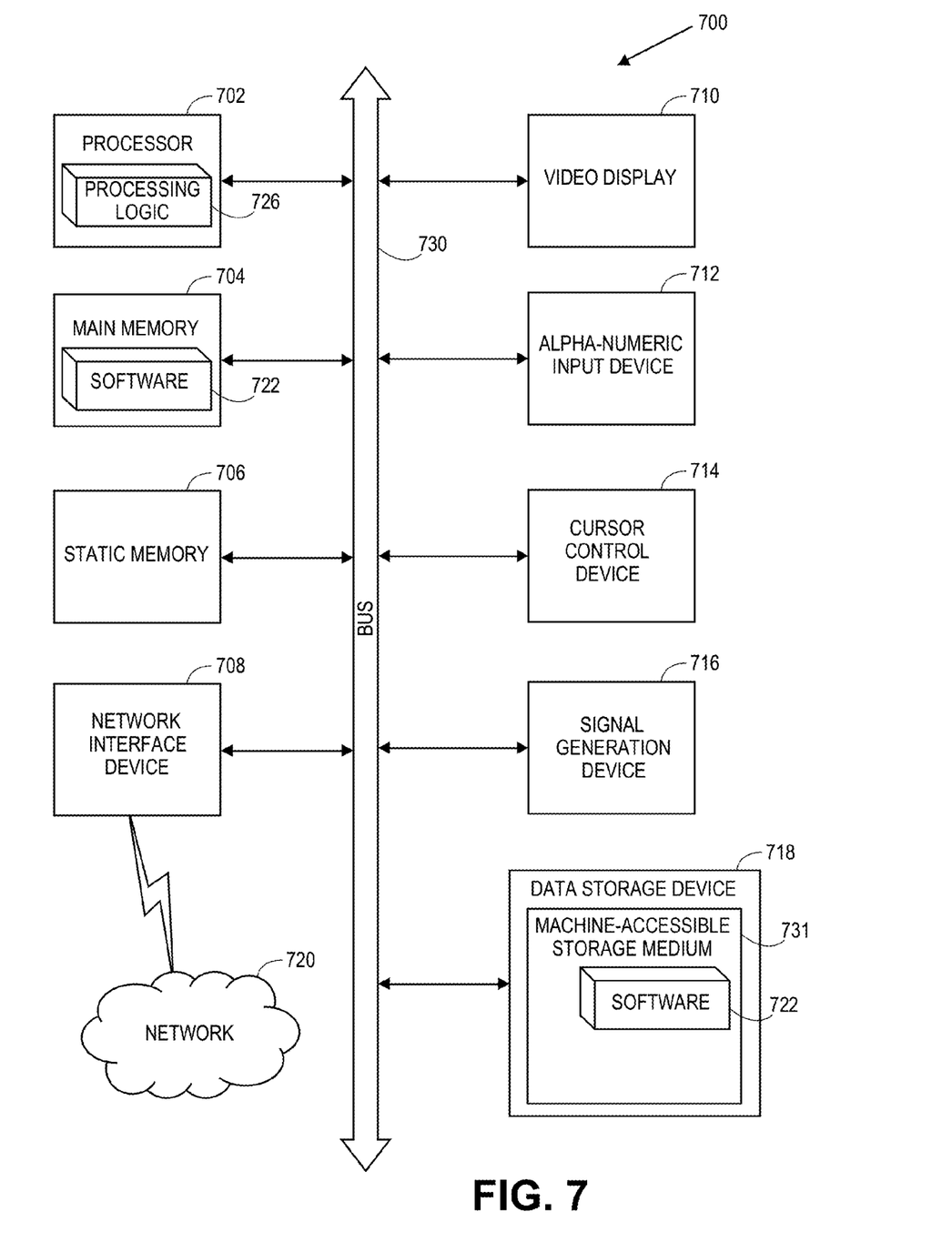
FIG. 7 illustrates a block diagram of an exemplary computer system for an apparatus used during the manufacture of an individual quartz crystal for ultimate monochromator fabrication, in accordance with an embodiment of the present invention.

FIG. 7 illustrates a diagrammatic representation of a machine in the exemplary form of a computer system 700 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. For example, in an embodiment, a machine is configured to execute one or more sets of instruction for fabricating a platelet for a monochromator.

The exemplary computer system 700 includes a processor 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a secondary memory 718 (e.g., a data storage device), which communicate with each other via a bus 730.

Processor 702 represents one or more general-purpose processing devices such as a microprocessor, central processing unit, or the like. More particularly, the processor 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 702 may also be one or more special-purpose processing devices such as an application specific integrated circuit (ASIC), a field programmable gate array (FPGA), a digital signal processor (DSP), network processor, or the like. Processor 702 is configured to execute the processing logic 726 for performing the operations discussed herein.

The computer system 700 may further include a network interface device 708. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), and a signal generation device 716 (e.g., a speaker).

The secondary memory 718 may include a machine-accessible storage medium (or more specifically a computer-readable storage medium) 731 on which is stored one or more sets of instructions (e.g., software 722) embodying any one or more of the methodologies or functions described herein. The software 722 may also reside, completely or at least partially, within the main memory 704 and/or within the processor 702 during execution thereof by the computer system 700, the main memory 704 and the processor 702 also constituting machine-readable storage media. The software 722 may further be transmitted or received over a network 720 via the network interface device 708.

While the machine-accessible storage medium 731 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a computer system has a non-transitory machine-accessible storage medium having instructions stored thereon which cause a data processing system to perform a method of fabricating a platelet of a monochromator for X-ray photoelectron spectroscopy. The method involves measuring, by X-ray reflection, an orientation of a crystal plane of the crystal, the crystal plane beneath a top surface of the crystal and having a primary axis. The method also involves, measuring a surface angle of the top surface of the crystal by measuring a light beam reflected from a reflective layer disposed on the top surface of the crystal. In one such embodiment, the surface angle of the top surface of the crystal is measured while measuring the orientation of the crystal plane by X-ray reflection.

Thus, methods and systems for fabricating platelets of a monochromator for X-ray photoelectron spectroscopy (XPS) have been described.

What is claimed is:

1. A method of fabricating a platelet of a monochromator for X-ray photoelectron spectroscopy, the method comprising:
    placing a crystal on a stage of an X-ray measuring apparatus, the crystal having a top surface;
    measuring, by X-ray reflection, an orientation of a crystal plane of the crystal, the crystal plane beneath the top surface of the crystal and having a primary axis; and
    measuring a surface angle of the top surface of the crystal by measuring a light beam reflected from the top surface of the crystal.

2. The method of claim 1, wherein a reflective layer is disposed on the top surface of the crystal, and wherein measuring the surface angle of the top surface of the crystal comprises measuring the light bean reflected from the reflective layer.

3. The method of claim 1, further comprising:
    determining an angle between the top surface and the primary axis of the crystal plane of the crystal.

4. The method of claim 3, further comprising:
    if the angle between the top surface and the primary axis of the crystal plane of the crystal is approximately normal, fabricating a monochromator comprising the platelet.

5. The method of claim 4, further comprising:
    prior to fabricating the monochromator, thinning a bottom surface of the crystal to render the bottom surface parallel with the top surface based on interferometric feedback.

6. The method of claim 3, further comprising:
    if the angle between the top surface and the primary axis of the crystal plane of the crystal is non-normal, removing at least a portion of the top surface of the crystal to provide a modified crystal having a second top surface;
    measuring, by X-ray reflection, an orientation of a crystal plane of the modified crystal, the crystal plane beneath the second top surface of the modified crystal; and, while measuring the orientation of the crystal plane by X-ray reflection,
    measuring a surface angle of the second top surface of the modified crystal by measuring a light beam reflected from the second top surface of the modified crystal; and
    determining an angle between the second top surface and the crystal plane of the modified crystal.

7. The method of claim 6, wherein removing the portion of the top surface of the crystal comprises polishing the top surface of the crystal.

8. The method of claim 6, further comprising:
thinning, from a bottom surface of the modified crystal opposite the second top surface, the modified crystal to render the bottom surface parallel with the second top surface based on interferometric feedback.

9. The method of claim 2, wherein the crystal is a quartz crystal, and the reflective layer is a layer comprising silver.

10. The method of claim 1, wherein measuring the light beam reflected from the top surface comprises impinging radiation from a light source of an autocollimator on the top surface.

11. The method of claim 10, wherein the impinging radiation from the light source of the autocollimator comprises aligning the radiation normal to the stage of the X-ray measuring apparatus.

12. The method of claim 10, wherein impinging radiation from the light source of the autocollimator comprises impinging visible light from the light source of the autocollimator.

13. The method of claim 1, wherein measuring the light beam reflected from the top surface comprises impinging radiation from a light source at an angle oblique to the stage of the X-ray measuring apparatus.

14. The method of claim 1, wherein placing the crystal on the stage of the X-ray measuring apparatus comprises using an imperfect stage.

15. The method of claim 1, wherein measuring the surface angle of the top surface of the crystal comprises accommodating for rocking of the crystal on the stage during the measuring of the orientation of the crystal plane of the crystal.

16. The method of claim 1, wherein measuring the orientation of the crystal plane of the crystal comprises performing first and second X-ray reflection measurements at approximately 180 degrees to one another.

17. The method of claim 16, wherein measuring the orientation of the crystal plane of the crystal further comprises performing third and fourth X-ray reflection measurements at approximately 180 degrees to one another, and orthogonal to the first and second X-ray reflection measurements.

18. The method of claim 1, wherein measuring the surface angle of the top surface of the crystal is performed while measuring the orientation of the crystal plane by X-ray reflection.

* * * * *